US012734010B2

(12) United States Patent
Zhang

(10) Patent No.: US 12,734,010 B2
(45) Date of Patent: Sep. 15, 2026

(54) GUIDING AND POSITIONING STRUCTURE FOR STERILE ADAPTER AND BACK END OF SURGICAL INSTRUMENT

(71) Applicant: CORNERSTONE TECHNOLOGY (SHENZHEN) LIMITED, Shenzhen (CN)

(72) Inventor: Jianwei Zhang, Shenzhen (CN)

(73) Assignee: CORNERSTONE TECHNOLOGY (SHENZHEN) LIMITED, Shenzhen (CN)

( * ) Notice: Subject to any disclaimer, the term of this patent is extended or adjusted under 35 U.S.C. 154(b) by 255 days.

(21) Appl. No.: 18/409,685

(22) Filed: Jan. 10, 2024

(65) Prior Publication Data

US 2024/0138950 A1 May 2, 2024

Related U.S. Application Data

(63) Continuation of application No. PCT/CN2022/100532, filed on Jun. 22, 2022.

(30) Foreign Application Priority Data

Jul. 14, 2021 (CN) ......................... 202110796258.7

(51) Int. Cl.
*A61B 90/00* (2016.01)
*A61B 34/30* (2016.01)

(52) U.S. Cl.
CPC .............. *A61B 90/08* (2016.02); *A61B 34/30* (2016.02)

(58) Field of Classification Search
CPC .................... A61B 90/08; A61B 34/30; A61B 2018/00172; A61B 2017/00398;
(Continued)

(56) References Cited

U.S. PATENT DOCUMENTS

2013/0110129 A1 5/2013 Reid et al.
2017/0367782 A1 12/2017 Schuh et al.
(Continued)

FOREIGN PATENT DOCUMENTS

AT 90979 B 1/1923
CN 105611893 A 5/2016
(Continued)

OTHER PUBLICATIONS

Cornerstone Technology (Shenzhen) Limited, European Communication pursuant to Article 94(3) Epc, EP22841148.4, Oct. 21, 2025, 8 pgs.

(Continued)

*Primary Examiner* — Carl H Layno
*Assistant Examiner* — Mary Grace Schlueter
(74) *Attorney, Agent, or Firm* — ScienBiziP, P.C.

(57) ABSTRACT

The present disclosure discloses a guided positioning structure for a sterile adapter and a back end of a surgical instrument. The sterile adapter includes a backboard perpendicular to an upper surface of a body structure of the sterile adapter, the backboard is coupled to the back end of the surgical instrument, and the backboard includes a portion for guiding the back end of the surgical instrument to move in a first direction and a portion for guiding the back end of the surgical instrument to move in a second direction. The guiding and positioning structure for the sterile adapter and the back end of the surgical instrument in the present disclosure limits the range of movement of the back end of the surgical instrument to a smaller width and amplitude when the back end of the surgical instrument is mounted to fit with the sterile adapter.

20 Claims, 7 Drawing Sheets

(58) Field of Classification Search

CPC .... A61B 2017/00477; A61B 2034/305; A61B 34/70; A61B 17/00; A61B 2034/302; A61B 34/35; A61B 34/37; A61B 34/71; A61B 46/10

USPC ........................................................ 606/1, 130

See application file for complete search history.

(56) References Cited

U.S. PATENT DOCUMENTS

| | | | |
|---|---|---|---|
| 2018/0140366 A1 | 5/2018 | Kapadia | |
| 2018/0200021 A1 | 7/2018 | Scheib et al. | |
| 2018/0221095 A1* | 8/2018 | Bailey | A61B 90/11 |
| 2019/0151037 A1 | 5/2019 | Steger | |
| 2020/0069385 A1 | 3/2020 | Ago et al. | |
| 2020/0069390 A1 | 3/2020 | Betsugi et al. | |

FOREIGN PATENT DOCUMENTS

| | | | |
|---|---|---|---|
| CN | 111374771 A | 7/2020 | |
| CN | 111547250 A | 8/2020 | |
| CN | 112022244 A * | 12/2020 | A61B 34/35 |
| CN | 113349936 A | 9/2021 | |
| CN | 113349937 A | 9/2021 | |
| CN | 216702631 U | 6/2022 | |
| JP | 2019122769 A | 7/2019 | |

OTHER PUBLICATIONS

Cornerstone Technology (Shenzhen) Limited, Extended European Search Report, EP 22841148.4, Aug. 29, 2024, 28 pgs.

Cornerstone Technology (Shenzhen) Limited, International Search Report with English translation, PCT/CN2022/100532, Sep. 27, 2022, 10 pgs.

Cornerstone Technology (Shenzhen) Limited, Cn Second Office Action with English translation, CN 2021107962587, Jan. 5, 2026, 14 pgs.

* cited by examiner

GUIDING AND POSITIONING STRUCTURE FOR STERILE ADAPTER AND BACK END OF SURGICAL INSTRUMENT

CROSS REFERENCE TO RELATED APPLICATIONS

The present application is a continuation of PCT Patent Application No. PCT/CN2022/100532, filed Jun. 22, 2022, which claims priority to Chinese Patent Application No. 202110796258.7, entitled "GUIDING AND POSITIONING STRUCTURE FOR STERILE ADAPTER AND BACK END OF SURGICAL INSTRUMENT," filed Jul. 14, 2021, each of which is incorporated by reference herein in its entirety.

TECHNICAL FIELD

The present disclosure relates to the technical field of medical devices, and more specifically to a guiding and positioning structure for a sterile adapter and a back end of a surgical instrument.

BACKGROUND

Surgical robots have a large number of applications in clinical surgery as they help surgeons achieve precise positioning for surgery, have advantages such as reducing patient's wounds and thereby shortening post-operative recovery time, and have a stable operating platform capable of addressing situations such as tremors of surgeons.

A surgical instrument in the surgical robot typically has an end effector in the form of a surgical tool, such as forceps, scissors, clamps, etc., at one end of an elongated tube. In general, wires or ropes are employed to manipulate the end effector to pitch, yaw and grip.

A surgeon controls, at a console side, the instrument connected to a drive at a surgical side. In order to meet demands for different surgical instruments to be used during surgery, surgical instruments and the instrument drive are typically designed to be detachable for changing different surgical instruments during the surgery, and the surgical instruments are typically sterilized independently.

The instrument drive is typically designed to be non-sterilizable, and in order to ensure sterility during the surgery, a sterile adapter needs to be added between the instrument drive and the instrument during the surgery to isolate the non-sterilizable instrument drive and the sterilizable instrument during the surgery.

A back end of the surgical instrument is connected to an upper surface of the sterile adapter, the instrument drive is connected to a lower surface of the sterile adapter, and the instrument drive provides a driving force to the end effector of the surgical instrument through the sterile adapter for achieving pitch, yaw and grip of the end effector.

The lower surface of the sterile adapter is connected to an upper surface of the instrument drive, which are stable and undetached after connection, and meanwhile, the sterile adapter is also able to be easily and quickly unlocked and detached from the instrument drive when needed. The back end of the surgical instrument is connected to the upper surface of the sterile adapter, which are stable and undetached after connection, and meanwhile, the surgical instrument is also able to be easily and quickly unlocked and detached from the sterile adapter when needed.

In conventional surgical robots, a guiding structure of the sterile adapter is a complete arc-shaped surface. During installation, the arc-shaped surface causes a surgical instrument box to rotate about a Z direction, so that an operator needs to pay more attention to the rotation and deflection of a lower end of a shaft of the surgical instrument to see if it is able to be accurately inserted into a cannula in a patient's abdomen and if it collides with the cannula in the patient's abdomen, and then to adjust a rotation angle of the surgical instrument box for further precise guidance. This method requires the operator to calibrate back and forth between upper and lower ends of the surgical instrument during installation, which distracts the operator and needs more operations for installation.

SUMMARY

A series of simplified concepts are introduced in the summary section, which will be further elaborated in the embodiments. The summary section of the present disclosure is not intended to limit the key features and essential technical features of the claimed technical solution, let alone to determine the protection scope of the claimed technical solution.

Embodiments of the present disclosure provide a guiding and positioning structure for a sterile adapter and a back end of a surgical instrument, including a backboard on the sterile adapter, where the backboard is perpendicular to an upper surface of a body structure of the sterile adapter; where the backboard is configured to be coupled to the back end of the surgical instrument, and the backboard includes a portion for guiding the back end of the surgical instrument to move in a first direction and a portion for guiding the back end of the surgical instrument to move in a second direction; and where the first direction traverses the second direction.

The guiding and positioning structure for the sterile adapter and the back end of the surgical instrument provided in the embodiments of the present disclosure limits a range of movement of the back end of the surgical instrument to a smaller width and amplitude during installation of the back end of the surgical instrument to the sterile adapter, so that the back end of the surgical instrument has a smaller range of movement throughout the whole installation process, which avoids deflection or a large oscillation of a forward end or a lower end of the surgical instrument, thereby avoiding distracting the operator's attention during operation.

In an embodiment, the backboard includes a portion for limiting the back end of the surgical instrument from moving in the first direction.

In an embodiment, the backboard includes a portion for limiting the back end of the surgical instrument from moving in the second direction.

In an embodiment, the backboard has a surface configured to contact the back end of the surgical instrument, the back end of the surgical instrument has a surface configured to contact the backboard, one of the surfaces of the backboard and the back end defines at least one groove, and the other one of the surfaces of the backboard and the back end is provided with at least one protrusion fitting with partly the at least one groove; where each of the at least one groove includes a portion having a width that is in the first direction and reduces in a third direction; and where the first direction, the second direction and the third direction traverse each other.

In an embodiment, each of the at least one groove includes a portion having a width that is in the first direction and is constant in the third direction, and the at least one protrusion at least partly fits with the portion having the constant width of the respective groove.

In an embodiment, the at least one groove is defined on the backboard, each of the at least one groove has an upper portion and a lower portion, and a width in the first direction of the upper portion is greater than a width in the first direction of the lower portion.

In an embodiment, the lower portion of each of the at least one groove has a width that is in the first direction and is constant in the third direction.

In an embodiment, the backboard defines two grooves, the backboard further has an adjoining surface between the two grooves, and a width in the second direction of an upper portion of the adjoining surface is less than a width in the second direction of a lower portion of the adjoining surface.

In an embodiment, the lower portion of the adjoining surface includes a portion having a width that is in the second direction and is constant in the third direction.

In an embodiment, the sterile adapter is engaged with the back end of the surgical instrument, and the sterile adapter and the back end of the surgical instrument each includes a fitting surface at a location where the sterile adapter and the back end of the surgical instrument are engaged with each other. In this embodiment, one the one hand, the use of the engagement location of the sterile adapter and the back end of the surgical instrument for precise guiding and precise positioning further enables precise guiding and positioning of the docking of the sterile adapter and the surgical instrument, on the other hand, a plurality of different mechanisms cooperate with each other to achieve better effects.

In an embodiment, the sterile adapter includes a plurality of hooks protruding from the upper surface, the back end of the surgical instrument has a lower surface on which a plurality of recesses are defined, and each of the plurality of hooks has an outer surface fitted to a respective one of the plurality of recesses of the back end of the surgical instrument.

In an embodiment, a fitting surface of each of the plurality of hooks and each of the plurality of recesses includes a plurality of curved surfaces, a plurality of straight surfaces, or a combination of at least one of the plurality of curved surfaces and at least one of the plurality of straight surfaces.

In an embodiment, each of the plurality of hooks includes an upper end having a first guiding surface extending to a left side and a right side of each of the plurality of hooks.

In an embodiment, each of the plurality of hooks includes an upper end having a second guiding surface extending to a front side and a rear side of each of the plurality of hooks.

In an embodiment, each of the plurality of hooks includes a lower end having a vertical positioning portion on a front side of each of the plurality of hooks.

In an embodiment, each of the plurality of hooks includes a lower end having a slope surface on a rear side of each of the plurality of hooks.

In an embodiment, each of the plurality of hooks includes a lower end having a fitting portion on each of a left side and a right side of each of the plurality of hooks.

BRIEF DESCRIPTION OF THE DRAWINGS

In order to more clearly illustrate the technical solutions in the embodiments of the present disclosure, the accompanying drawings to be used in the embodiments of the present disclosure are briefly described below. For those of ordinary skill in the art, other accompanying drawings are able to be obtained based on these drawings without creative efforts.

DETAILED DESCRIPTION OF THE EMBODIMENTS

Figure 1:
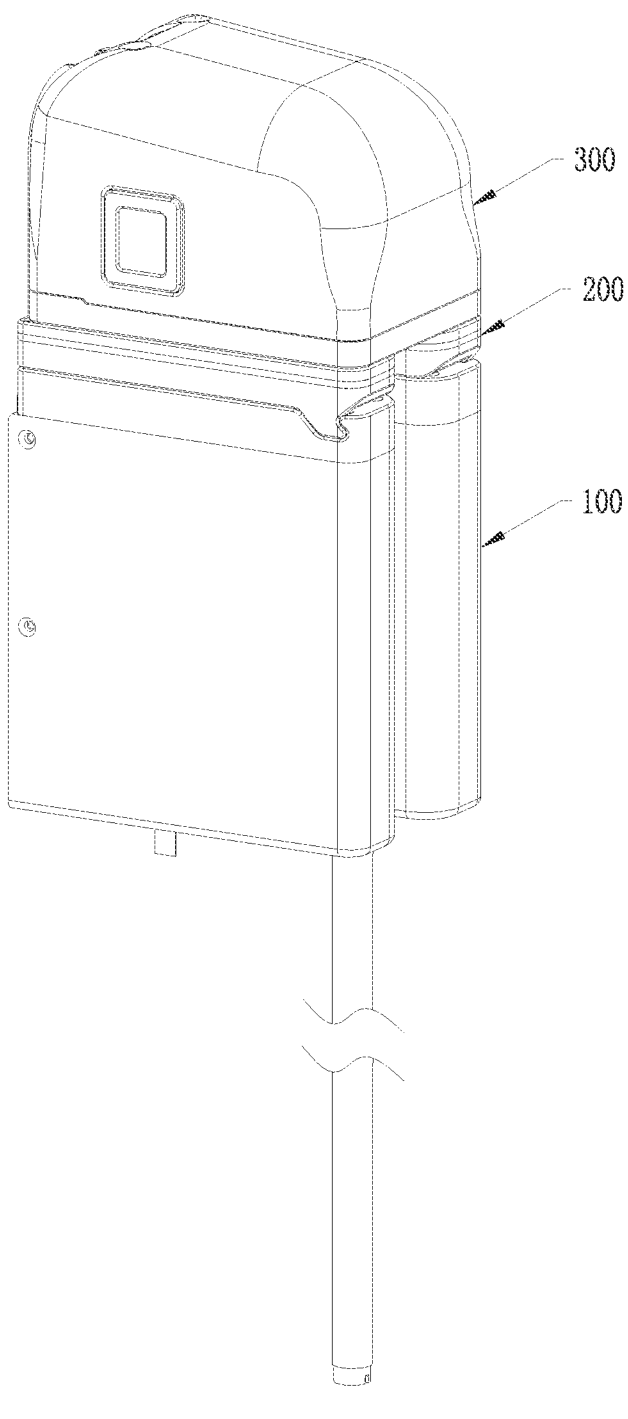
FIG. 1 is a schematic structural diagram of an instrument drive, a sterile adapter and a surgical instrument in an assembly completion state provided in an embodiment of the present disclosure.
Figure 2:
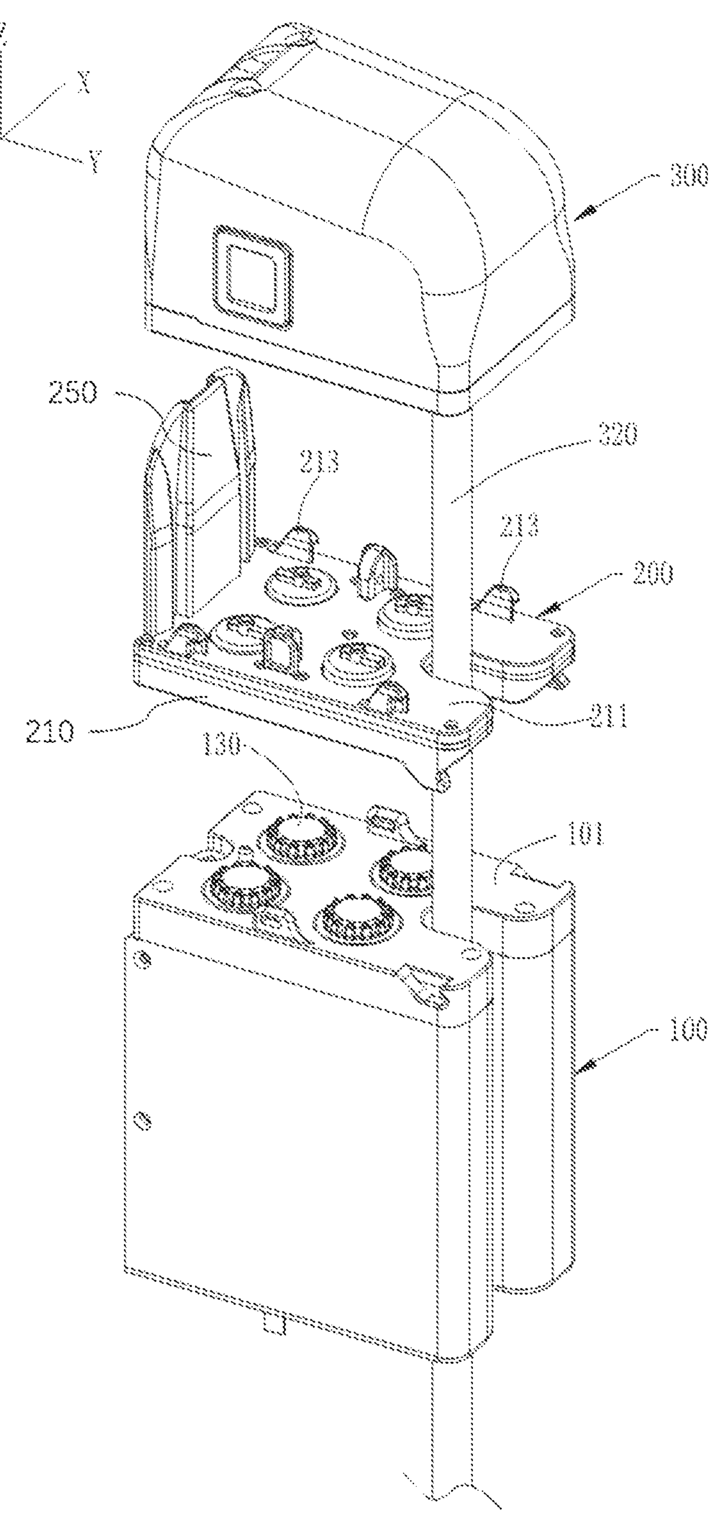
FIG. 2 is a schematic diagram of an instrument drive, a sterile adapter, and a surgical instrument in a disassembled state provided in an embodiment of the present disclosure.

Features and exemplary embodiments of various aspects of the present disclosure will be described in detail below, and in order to make the purposes, technical solutions, and advantages of the present disclosure more clearly, the present disclosure is described in further detail below with reference to the accompanying drawings and embodiments. It should be understood that the embodiments described herein are provided only to explain the present disclosure and are not provided to limit the present disclosure. For those skilled in the art, the present disclosure is able to be implemented without some of these specific details. The following description of the embodiments is merely intended to provide a better understanding of the present disclosure by illustrating examples of the present disclosure.

It should be noted that terms such as 'first' and 'second' in the present disclosure are used only to distinguish one entity or operation from another, and do not necessarily require or imply the existence of any such actual relationship or order between these entities or operations. Furthermore, terms 'including', 'comprising', or any other variant thereof, are intended to cover non-exclusive inclusion, such that a process, method, article, or apparatus including a set of elements includes not only those elements, but also other elements not expressly listed, or other elements inherent to such process, method, article or apparatus. In the absence of further limitations, the element defined by the phrase 'including . . . ' does not preclude the existence of additional identical elements in the process, method, article or apparatus including this element.

The present disclosure provides a mechanism for mounting and fitting a surgical instrument, a sterile adapter and an instrument drive of a surgical robot. Embodiments of the present disclosure are described below with reference to the accompanying drawings.

In the present disclosure, a mechanism for realizing drive and transmission of the surgical instrument includes three main components, i.e., an instrument drive, a sterile adapter, and a surgical instrument.

First of all, a plurality of directional terms are defined in the embodiments to describe positional relationships between the components, and these directional terms are interpreted with a longitudinal direction of a shaft of the surgical instrument as a Z direction, a spanwise direction of a backboard of the sterile adapter as an X direction, and a direction from the backboard of the sterile adapter to the shaft of the surgical instrument as a Y direction. Terms 'upper' and 'lower' are indicative of visual angles of the instrument drive, the sterile adapter, and the surgical instrument during use. Terms 'front' and 'rear' are indicative of directions based on the shaft of the surgical instrument and the rear of the surgical instrument box, in which a position of the shaft of the surgical instrument is "front", and a position of the rear of the surgical instrument box is "rear". Terms 'left' and 'right' are indicative of left and right directions based on two opposite sides of the surgical instrument box as seen from a viewpoint looking directly at the shaft of the surgical instrument.

As shown in FIGS. 1, 2, 5, and 8, the instrument drive 100, the sterile adapter 200, and the surgical instrument 300, in turn, have adapted structures on upper and lower surfaces (i.e., XY surfaces) such that an upper surface of the instrument drive 100, an upper surface 211 of the sterile adapter 200, a lower surface of the sterile adapter 200, and a lower surface of the surgical instrument box 310 are not visible after assembly.

The instrument drive 100 is mounted on a sliding arm of a robotic arm of the surgical robot and is able to move up and down on the sliding arm. A drive motor outputs power through an output shaft and corresponding transmission members connected to the output shaft. Specifically, the instrument drive 100 has a regularly shaped housing with a plurality of drive motors inside the instrument, which may be three, four, or five, etc., and each of the drive motors is correspondingly connected to an output shaft, so that the number of output components of the instrument drive 100 corresponds to the number of drive motors. An upper portion of the instrument drive 100 is an assembly surface 101 capable of being connected to an assembly surface of the sterile adapter 200.

The assembly surface 101 of the instrument drive 100 is provided with mounting holes for the output components of the driver. In the embodiments, the output components of the instrument drive 100 includes a plurality of driver transmissions 130, each of the plurality of driver transmissions 130 is disposed within each respective mounting hole, and an upper end of each of the plurality of driver transmissions 130 protrudes from the assembly surface 101 of the instrument drive 100.

The sterile adapter 200 isolates the instrument drive 100 from direct contact with the surgical instrument 300 by being attached to a sterile enclosure curtain. The sterile enclosure curtain and the sterile adapter 200 wrap the robotic arm of the surgical robot and the instrument drive 100 to isolate them from the outside, the sterile adapter 200 is engaged to an upper surface of the instrument drive 100, and the sterile adapter 200 is provided with a plurality of adapter transmissions 230 to transmit power.

The sterile adapter 200 has a body structure 210, the lower surface of the body structure 210 is fitted to the assembly surface 101 of the instrument drive 100, and the upper surface 211 of the body structure 210 is fitted to the surgical instrument 300. The body structure 210 is provided with adapter transmission mounting holes penetrating through the top and bottom of the body structure 210, and each adapter transmission 230 is disposed within a respective adapter transmission mounting hole such that a lower portion of each adapter transmission 230 is fitted to an upper end of each of a plurality of instrument transmissions 311, and an upper portion of each adapter transmission 230 is fitted to a lower end of each instrument transmission 311.

The surgical instrument 300 includes a surgical instrument box 310 at a back end and an effector (not shown) at a forward end, and an instrument shaft 320 connected between the surgical instrument box 310 and the effector. The surgical instrument box 300 is engaged with the sterile adapter 200 and is fitted to the plurality of adapter transmissions 230 of the sterile adapter 200 via the plurality of instrument transmissions 311 of the surgical instrument 300. The instrument drive 100 drives the movement of the surgical instrument 300 for pitching, deflecting and gripping.

In some embodiments, the sterile adapter 200 and the instrument drive 100 have a connection for non-transmission in addition to a connection for transmission, and the connection for the non-transmission is in the form of snap connection.

Similarly, the surgical instrument 300 and the sterile adapter 200 have a connection for non-transmission, i.e., the surgical instrument 300 is connected to the sterile adapter 200 via hooks.

Before the surgical instrument 300 is snap-fit to the sterile adapter 200, the mounting of the surgical instrument 300 and the sterile adapter 200 needs to be guided. The following describes in detail a guiding and positioning structure for the surgical instrument 300 and the sterile adapter 200.

Embodiments of the present disclosure provide a guiding and positioning structure for the sterile adapter and the surgical instrument box. Specifically, the guiding and positioning structure includes a backboard 250 placed on a rear side of the body structure 210 of the sterile adapter 200 and perpendicular to the upper surface 211 of an upper shell of the sterile adapter 200. The backboard 250 has a side surface facing the surgical instrument 300, i.e., a front side surface of the backboard 250, which interfaces with a rear side of the surgical instrument box 310. The backboard 250 also has a rear side surface adhesive with a sterile cloth along an edge of the backboard 250 to isolate the sterile cloth from the surgical instrument 300, or the rear side surface exist in isolation while the sterile cloth is adhesive with the body structure 210 of the sterile adapter 200.

On the one hand, the backboard 250 isolates the surgical instrument 300 from the sterile cloth to avoid frictional damage to the sterile cloth due to contact between the surgical instrument 300 and the sterile cloth. On the other hand, the backboard 250 plays a role of guide limitation during mounting.

Figure 3:
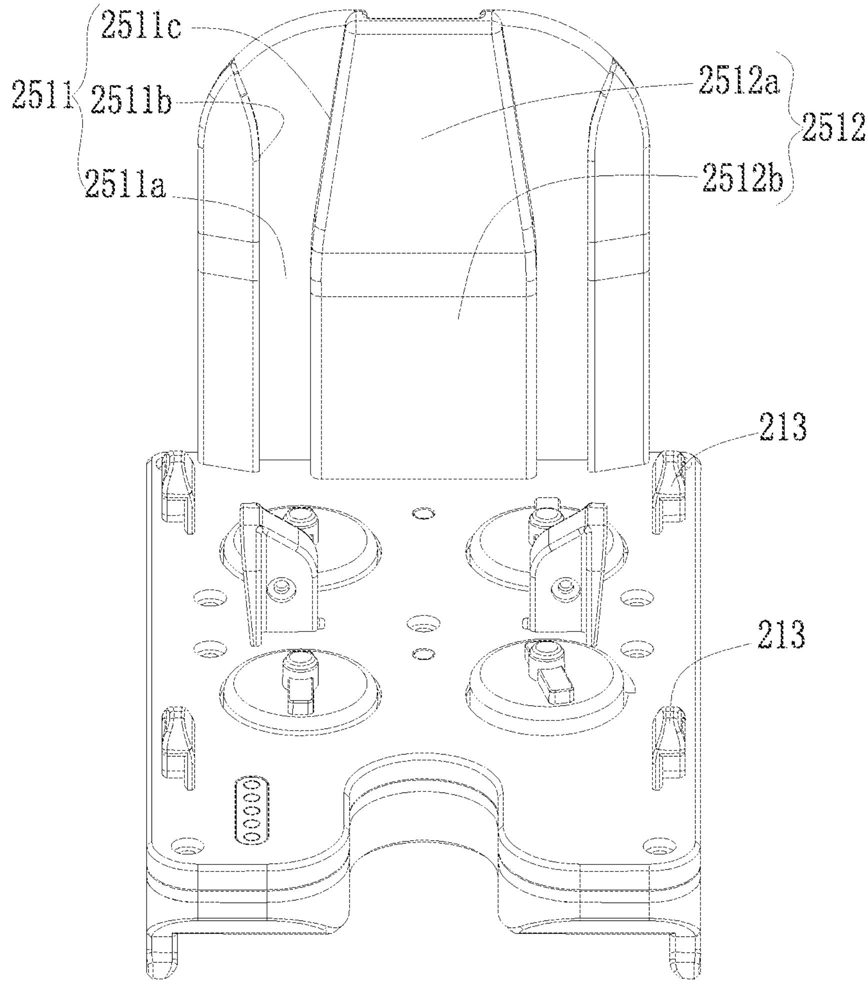
FIG. 3 is a three-dimensional view of a sterile adapter provided in an embodiment of the present disclosure.
Figure 4:
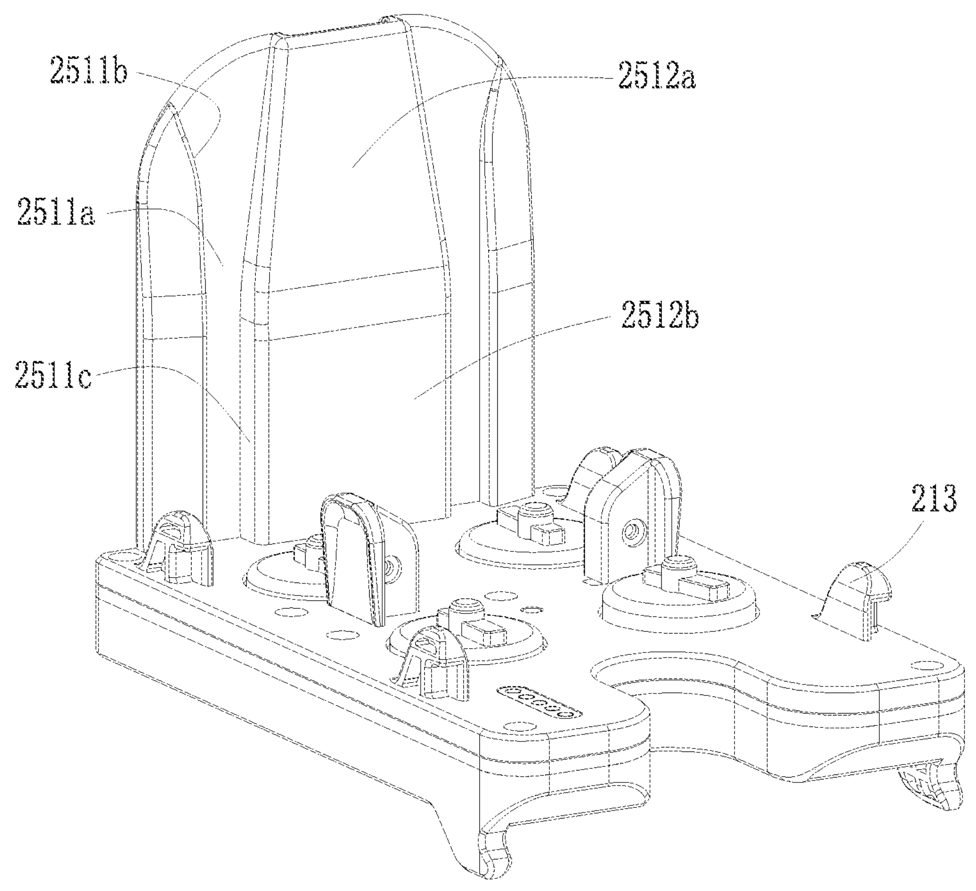
FIG. 4 is a three-dimensional view of a sterile adapter from another perspective provided in an embodiment of the present disclosure.
Figure 5:
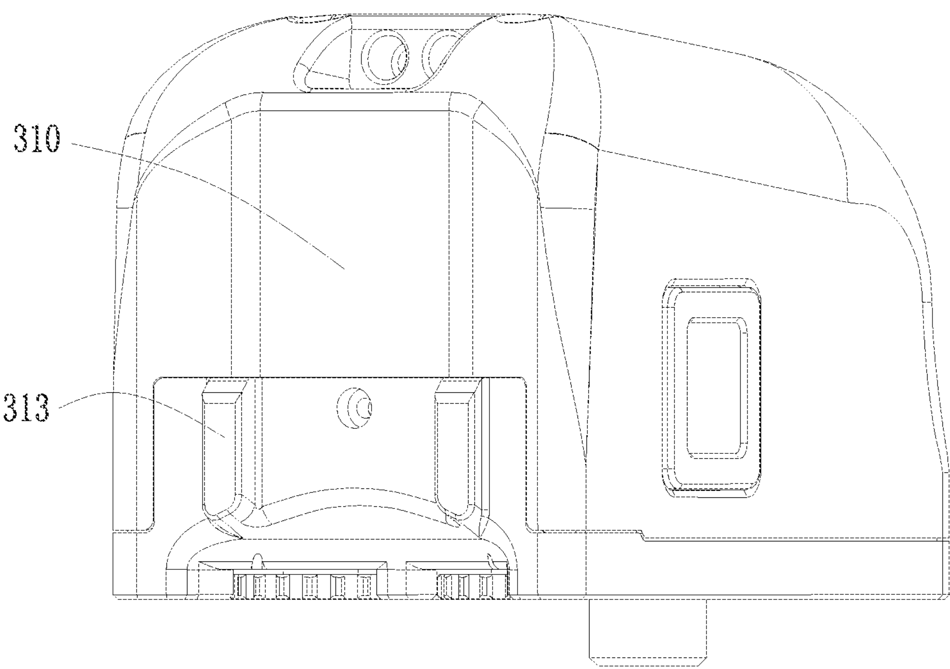
FIG. 5 is a three-dimensional view of a structure of a back end of a surgical instrument box provided in an embodiment of the present disclosure.

Specifically, referring to FIGS. 3, 4, and 5, a body of the backboard 250 is a plate-like structure, and guiding grooves 2511 running through from top to bottom of the backboard 250 are defined on the front side surface of the backboard 250. The surgical instrument box 310 includes protrusions 313 each capable of fitting with a respective guiding groove 2511, i.e., a width of each protrusion 313 is not greater than a width of each guiding groove 2511. Each protrusion 313 is provided in such a way as to be perfectly fitted with a structure of a respective guiding groove 2511 or only with a lower portion of the guiding groove 2511. The guiding grooves 2511 have the structures running through from top to bottom, so that the surgical instrument 300 is mounted from top to bottom.

Each guiding groove 2511 includes a plane 2511*a* that is perpendicular to the upper surface of the sterile adapter 200, which is also an XZ plane. This XZ plane limits a respective protrusion 313 from moving in the Y direction, and when the surgical instrument 300 is mounted, the protrusion 313 directly abuts against a portion of the XZ plane without adjusting a mounting position in the Y direction.

With reference to FIGS. 2, 4, 5, 6, and 7, each guiding groove 2511 further includes a first wall 2511*b* and a second wall 2511*c* that are perpendicular to the XY plane. A distance between the first wall 2511*b* and the second wall 2511*c* along the Z direction from top to bottom has a changed part, i.e., the width of the guide groove 2511, along the Z direction from top to bottom, has a part varies from greater to lesser, i.e., this part of the width of the guide groove 2511 is gradually changed from wider to narrower. This part of the structure is able to guide the protrusion 313 to move in the X direction, i.e., there is a certain space in the X direction to allow the protrusion 313 to adjust its position. Besides, no more effort is required when the protrusion 313 is inserted into the guiding groove 2511. Meanwhile, the distance between the first wall 2511*b* and the second wall 2511*c* has an unchanged part, i.e., the width of the guiding groove 2511 is constant in this part. When the width of the guiding groove 2511 gradually decreases to be perfectly fitted to the protrusion 313, the width of the guiding groove 2511 no longer changes, i.e., the guiding groove 2511 limits the protrusion 313 from moving in the X direction, and the protrusion 313 continues to move downwardly in the Z direction.

In some embodiments, one guiding groove 2511 is defined, or two guiding grooves 2511 are defined. When two guiding grooves 2511 are defined, the two guiding grooves 2511 have a surface 2512 between them. In order to enable the surgical instrument 300 to be micro-adjusted in the Y direction, an upper portion 2512*a* of the surface 2512 is provided as a beveled face for guiding the surgical instrument 300 to move in the Y direction. A lower portion 2512*b* of the surface 2512 is provided as a vertical face, i.e., a face parallel to the XZ plane, for limiting the surgical instrument 300 from moving in the Y direction.

Accordingly, the guiding is also able to be accomplished by means of adjacent first walls 2511*b* and second walls 2511*c* of the two guiding grooves 2511, with the connecting surface between the two guiding grooves 2511.

The above is the preliminary guiding and preliminary positioning of the docking of the surgical instrument 300 and the sterile adapter 200. In some embodiments, the surgical instrument box 310 and the sterile adapter 200 may also be provided with precise guiding and precise positioning. In the present disclosure, the precise guiding and precise positioning are set up in conjunction with the connection structure of the non-transmission parts of the sterile adapter 200 and the surgical instrument box 310.

Figure 6:
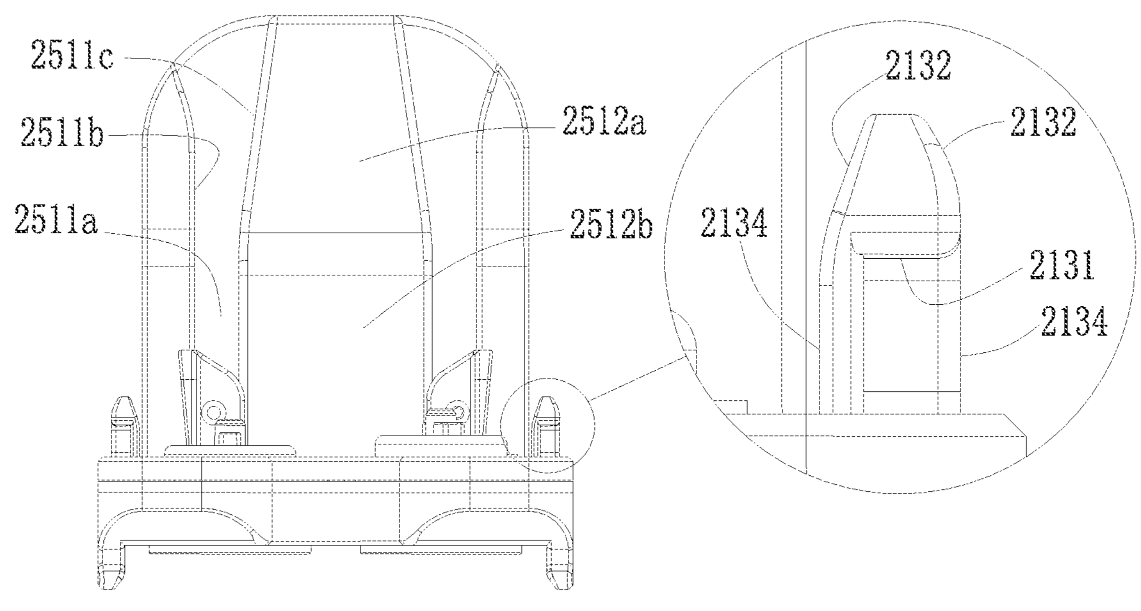
FIG. 6 is a front view of a sterile adapter provided in an embodiment of the present disclosure.
Figure 7:
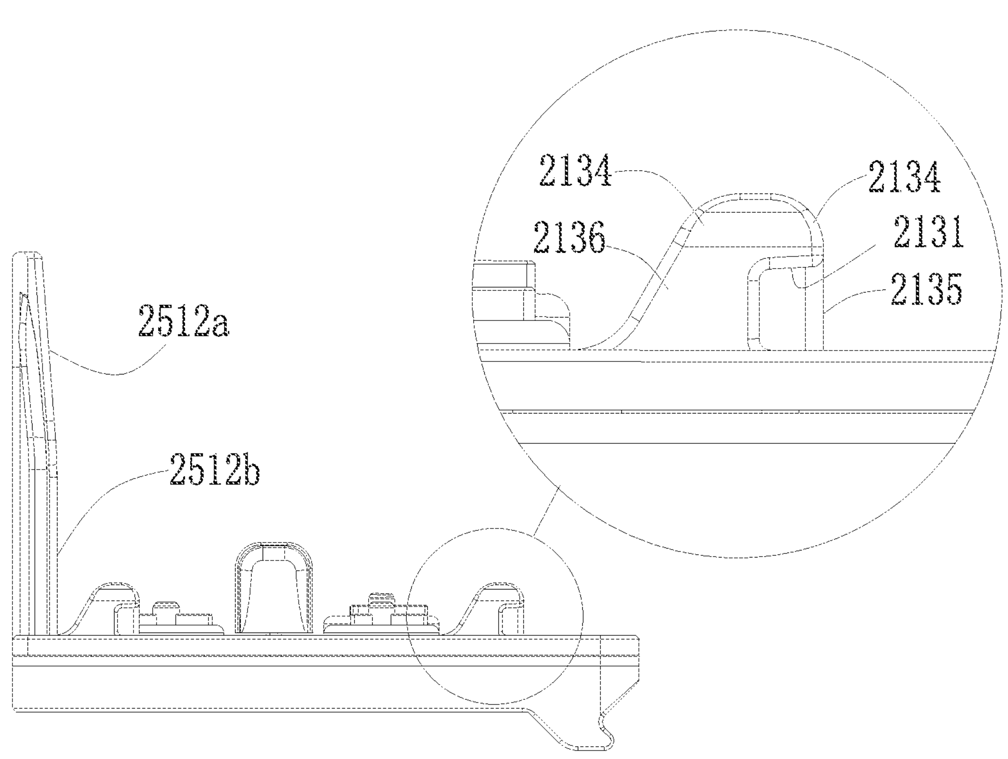
FIG. 7 is a side view of a sterile adapter provided in an embodiment of the present disclosure.
Figure 9:
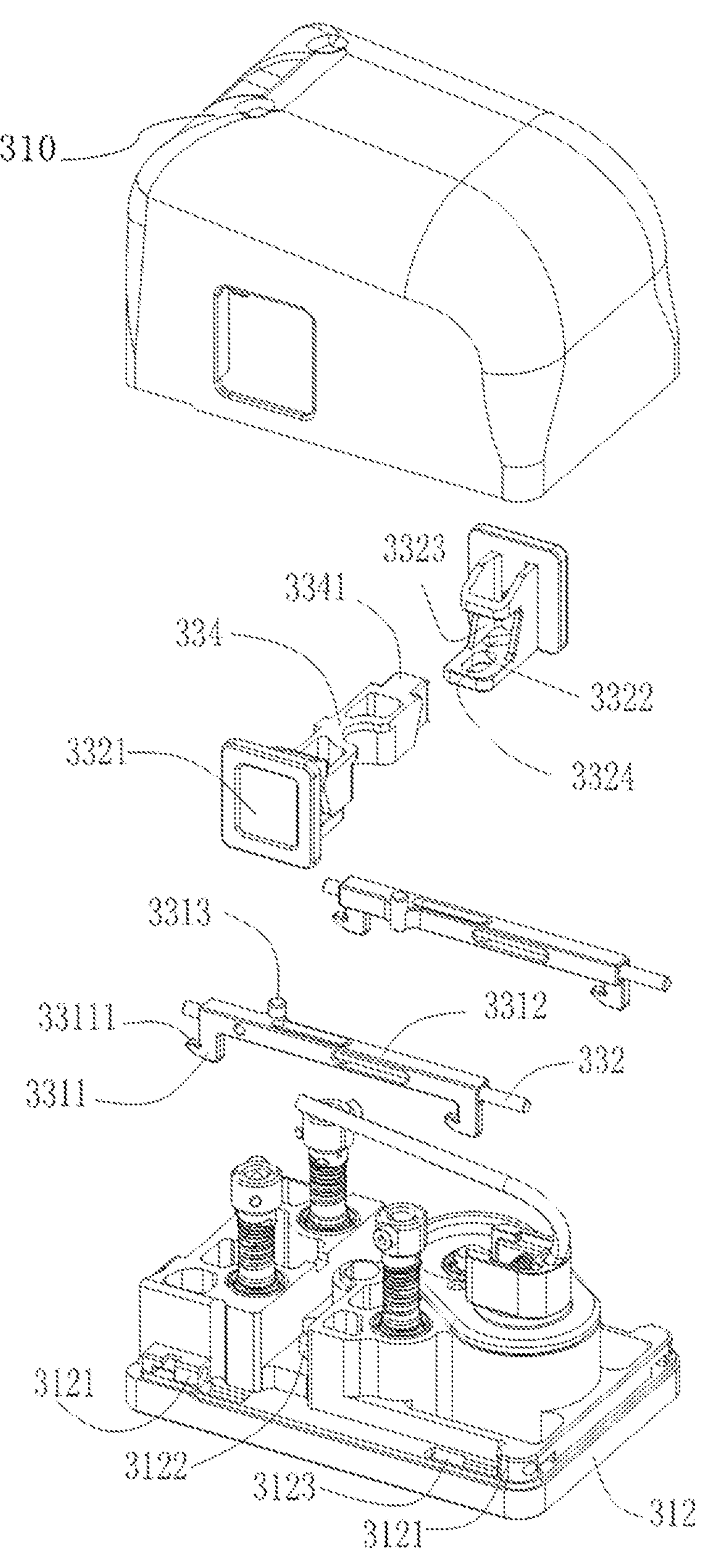
FIG. 9 is a schematic diagram of a disassembled structure of a movable hook assembly in a surgical instrument provided in an embodiment of the present disclosure.

Specifically, as shown in FIGS. 6, 7, and 9, the sterile adapter 200 and the surgical instrument box 310 are connected by means of a plurality of hooks 213 provided on the sterile adapter 200 and a plurality of movable hooks 3311 provided on the surgical instrument box 310, each of the plurality of movable hooks 3311 on the surgical instrument box 310 being snap-fit in a vertical direction to a respective hook 213 on the sterile adapter 200.

Specifically, the sterile adapter 200 includes the plurality of hooks 213 protruding from the upper surface 211. In some embodiments, two sets of hooks 213 are integrally molded with the upper shell of the sterile adapter 200. Each hook 213 of the sterile adapter 200 has a snap surface 2131, and the snap surface 2131 is oriented downward so that an upper portion of the hook 213 does not need to be connected with a respective movable hook 3311 of the surgical instrument box 310.

Specifically, each hook 213 has a smooth curved-surface structure in the X direction and Y direction at an upper end. In some embodiments, the upper end of each hook 213 is provided with a first guiding surface 2132 extending to left and right sides of the hook 213. The upper end of each hook 213 is provided with a second guiding surface 2133 extending to front and rear sides of the hook 213.

In some embodiments, the left and right sides of each hook 213 is provided with a fitting surface 2134 that is flat in a YZ plane.

In some embodiments, a lower end of the front side of each hook 213, i.e., a portion of the hook 213 adjacent to a front side of the sterile adapter 200, has a curvilinear surface around a Z axis, which is a vertical positioning portion 2135 of the hook 213.

In some embodiments, a lower end of the rear side of the hook 213, i.e., a portion of the hook 213 adjacent to the backboard 250, has a slope surface, which is a third guiding portion 2136 of the hook 213.

In some embodiments, the first guiding surface 2132, the second guiding surface 2133, the flat fitting surface 2134, the vertical positioning portion 2135 and the third guiding portion 2136 of the hook 213 are all in continuous smooth transition.

Figure 8:
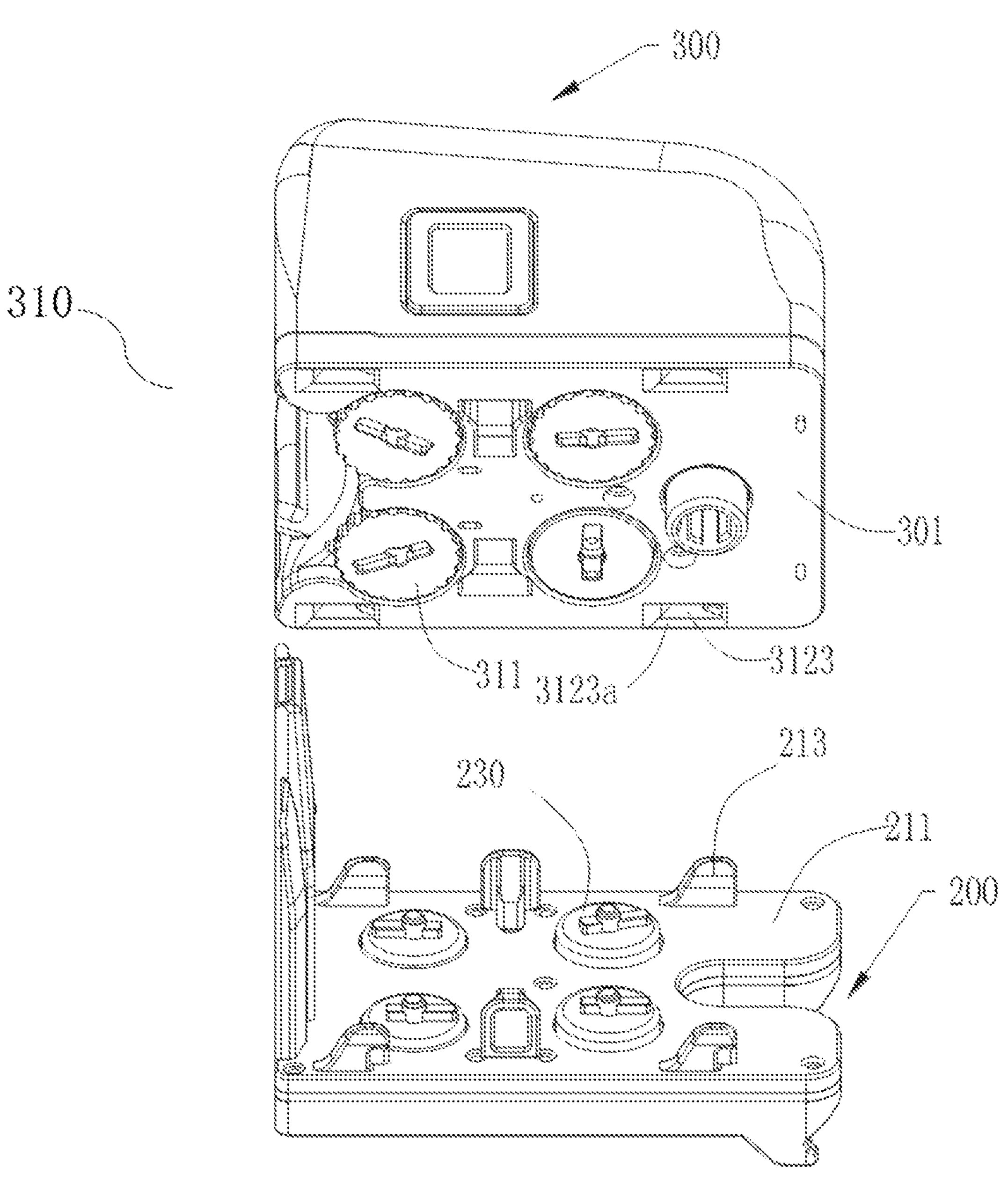
FIG. 8 is a disassembled view of a sterile adapter and a surgical instrument provided in an embodiment of the present disclosure.

Accordingly, as shown in FIG. 8, a plurality of recesses 3123 are defined on the lower surface 301 of the surgical instrument box 310 for the snap fit of the hooks, and each movable hook 3311 of the surgical instrument 300 is placed in a respective recess 3123. Each recess 3123 has smooth curved-surface structures in both the X direction and the Y direction, which is capable of being perfectly fitted to the hook 213.

In some embodiments, the smooth curved-surface structures in both the X direction and the Y direction are provided at an entrance 3123*a* of each recess 3123. The recess 3123 has a curved surface inside that is fitted to the upper end of the hook 213.

The hooks 213 of the sterile adapter 200 and the recesses 3123 of the surgical instrument 300 in the embodiments are not only capable of connecting the sterile adapter 200 and the surgical instrument 300, but also capable of guiding. Meanwhile, due to the fitting of surfaces of the sterile adapter 200 and the surgical instrument 300, there is a certain degree of rigidity in the surfaces that are fitted, which reduces to a certain extent the cumulative tolerance due to the movable snap-fit manner of the movable hooks 3311 and the hooks 213.

In some embodiments, further description is provided regarding the snap-fit relationship between the hooks 213 and the movable hooks 3311. Specifically, as in FIG. 9, two sets of hooks 213 are provided on the upper surface 211 of the sterile adapter 200, i.e., the two sets of hooks 213 are integrally molded with the upper shell of the sterile adapter 200. The surgical instrument box 310 includes a base 312 for mounting a steel wire pole, and a lower end of the steel wire pole is a drive connection for the surgical instrument 300. A movable hook assembly is provided on the base 312. The movable hook assembly includes the plurality of movable hooks 3311, and each movable hook 3311 has a snap surface 33111 facing upward, so that the movable hook 3311 is snap-fit to a respective hook 213 in the vertical direction.

The movable hook assembly includes movable members (not identified in the figures), each movable member includes two movable hooks 3311 and a connecting arm 3312 between the two movable hooks 3311. The connecting arm 3312 has a length such that the two movable hooks 3311 are disposed spaced apart from each other. Connecting arms 3312 of the two movable hooks are disposed on the left and right sides of the base, i.e., on the left and right sides inside the surgical instrument box 310. Each connecting arm 3312 extends in a direction along a front-rear direction, i.e., the Y direction, of the surgical instrument box 310. The connecting arm 3312 is fixedly connected to the two movable hooks 3311 so that the three become one.

Due to the limitation of the transmission portion within the surgical instrument box 310, a locked position and an unlocked position of each movable hook 3311 are limited to be located in a lengthwise direction of the connecting arm 3312, i.e., a movement direction of the movable hook 3311 is along the lengthwise direction of the connecting arm 3312. Specifically, the movable hook assembly further includes guiding rods 332, and both ends of each guiding rod 332 are fixedly connected to the base 312 via two guiding rod seats 3121. Each connecting arm 3312 defines a guiding groove (not shown) for a respective guiding rod 332 to pass through, and the guiding rod 332 passes through the guiding groove in the connecting arm 3312 to enable the connecting arm 3312 to move along the guiding rod 332. A distance between both ends of the guiding rod 332 is the maximum distance for the connecting arm 3312 to move. A spring (not shown) is provided at one end of each guiding rod 332 such that one end of the spring abuts against the connecting arm 3312 and the other end of the spring abuts against the guiding rod seat 3121. In a natural state, the driving force of the spring causes the connecting arm 3312 and the movable hook 3311 to be in the locked position. Accordingly, an opening direction of the snap surface 2131 of each hook 213 on the upper surface of the sterile adapter 200 is toward the direction of movement of the movable hook 3311. In some embodiments, the guiding rods 332 and the connecting arms 3312 are placed within the surgical instrument box 310, and as such, the recesses 3123 is provided on the base 312 to provide spaces for the movable hooks 3311 to move, as well as locations for being snap-fit to the hooks 213.

The movable hook assembly further includes operating portions. In some embodiments, each operating portion moves in a different direction than a direction of movement of a respective connecting arm 3312. That is, the operating portion is non-fixedly connected to the movable member. Specifically, each movable member has a passive portion 3313, and the passive portion 3313 is fixedly disposed on a respective connecting arm 3312. In some embodiments, the passive portion 3313 is integrally molded with other components of the movable member. Each operating portion includes an actuating portion 3322, and the actuating portion 3322 has an actuating surface such that a respective passive portion 3313 and the actuating surface are capable of forming line contact or surface contact, and the actuating surface of the actuating portion 3322 is capable of including a trajectory of the passive portion 3313. In some embodiments, the actuating surface is a beveled or curved surface and the passive portion 3313 includes a beveled or curved surface. The actuating surface has a component along the lengthwise direction of the connecting arm 3312 of the movable member and a component along a left-right direction of the surgical instrument 300. In some embodiments, the passive portion 3313 is provided as a bearing, and the passive portion 3313 rolls on the actuating surface of the actuating portion 3322.

In some embodiments, each operating portion further includes an operating button 3321, and the operating button 3321 is fixedly connected to a respective actuating portion 3322. The operating buttons 3321 are provided on both sides of the surgical instrument box 310 respectively, and the operating portions need to be pressed inwardly from both sides of the surgical instrument 300 during use, so that the operating portions move in a spanwise direction of the surgical instrument box 310, i.e., the X direction. This enables the force on each passive portion 3313 to break down the force along the front-rear direction of the surgical instrument box 310, i.e., the Y direction, so that each actuating portion 3322 drives a respective connecting arm 3312 as well as movable hooks 3311 to move in a direction of unlocking.

In some embodiments, the movable hook assembly further includes a guiding member 334 that assists in guiding the movement of the operating portion. Specifically, each operating portion further includes a guiding portion 3323, and the guide member 334 includes guiding portions 3341. Each guiding portion 3341 of the guiding member 334 has a number of fitting surfaces with the guiding portion 3323 of a respective operating portion in the spanwise direction of the surgical instrument box 310, i.e., guiding directions of the guiding member 334 and the guiding portion 3341 are the X direction. A spring (not shown) is further provided between the operating portion and the guiding member 334 such that one end of the spring abuts against the operating portion and the other end of the spring abuts against the guiding member 334.

In some embodiments, each operating portion is further provided with a limit waist hole 3324, and a respective limit pole 3122 is fixedly provided on the base 312. The limit pole 3122 passes through the limit waist hole 3324 in order to, on the one hand, avoid the operating portion from being detached from the surgical instrument box 310, and on the other hand, make the two sides of the limit waist hole 3324 to be unlocked and locked positions of the operating portion.

In some embodiments, the docking of the surgical instrument 300 with the sterile adapter 200 is performed as follows. The surgical instrument 300 is moved to the top of the sterile adapter 200 and the at least one protrusion 313 on the surgical instrument 300 respectively abuts against the plane of the at least one guiding groove 2511 of the backboard 250 of the sterile adapter 200, and then the surgical instrument 300 is moved downwardly along the at least one guiding groove 2511 until the upper portion of each the at least one guiding groove 2511 completes coarse guiding of the surgical instrument 300. The at least one protrusion 313 on the surgical instrument box 310 causes the back end of the surgical instrument 300 to no longer swing from side to side, and the surgical instrument 300 is coarsely positioned by the lower portion of each of the at least one guiding groove 2511 of the backboard 250 of the sterile adapter 200, and then the surgical instrument 300 continues to move downwardly. The entrance 3123*a* of each recess 3123 of the surgical instrument box 310 contacts the upper end of each hook 213 of the sterile adapter 200, and then the surgical instrument 300 is guided by the fitting of surfaces of each recess 3123 and each hook 213 to complete precise guiding so as to make the surgical instrument box 310 and the sterile adapter 200 accurately aligned. After that, the surgical instrument box 310 continues to move downward, accomplishing the snap fit between the movable member and the hooks 213, and then the surgical instrument box 310 and the sterile adapter 200 are mounted in place. The whole process is a continuous process, which does not require the user to spend much effort to adjust the position of the surgical instrument box 310, and is more convenient to use.

In accordance with the embodiments of the present disclosure as described above, these embodiments are not an exhaustive recitation of all the details and do not limit the present disclosure to only the specific embodiments described above. Apparently, many modifications and variations are able to be made in accordance with the foregoing description. These embodiments are selected and specifically described in the present disclosure for the purpose of better explaining the principles and practical applications of the present disclosure so that those skilled in the art are able to make good use of the present disclosure as well as modifications on the basis of the present disclosure. The present disclosure is limited only by the claims and their full scope and equivalents.

What is claimed is:

1. A sterile adapter operable with a surgical instrument, comprising a body structure and a backboard configured to be coupled to a back end of the surgical instrument, wherein the backboard is perpendicular to an upper surface of the body structure;

the backboard has a surface defining two indentations spaced apart from each other and a guiding surface between the two indentations;

a respective indentation of the two indentations is configured to accommodate a corresponding protrusion at the back end of the surgical instrument and has a planar surface configured to limit the corresponding protrusion from moving in a direction perpendicular to the planar surface, and a side wall connecting the planar surface and the guiding surface;

the side wall is configured to guide position adjustment of the surgical instrument in a first direction and to limit movement of the surgical instrument in the first direction;

the guiding surface has an upper beveled section configured to guide the surgical instrument to move in a second direction, and a lower limiting section configured to limit movement of the surgical instrument in the second direction;

the first direction traverses the second direction; and a plane defined by the first direction and the second direction is parallel to the upper surface of the body structure.

2. The sterile adapter according to claim 1, wherein the sterile adapter is engaged with the back end of the surgical instrument, and the sterile adapter and the back end of the surgical instrument each includes a fitting surface at a location where the sterile adapter and the back end of the surgical instrument are engaged with each other.

3. The sterile adapter according to claim 2, wherein the body structure of the sterile adapter includes a plurality of hooks protruding from the upper surface, the back end of the surgical instrument has a lower surface on which a plurality of recesses are defined, and each of the plurality of hooks has an outer surface shaped to fit a respective one of the plurality of recesses of the back end of the surgical instrument.

4. The sterile adapter according to claim 3, wherein a fitting surface of each of the plurality of hooks and each of the plurality of recesses includes a plurality of curved surfaces, a plurality of straight surfaces, or a combination of at least one of the plurality of curved surfaces and at least one of the plurality of straight surfaces.

5. The sterile adapter according to claim 3, wherein each of the plurality of hooks includes an upper end having a first guiding surface extending to a left side and a right side of each of the plurality of hooks.

6. The sterile adapter according to claim 3, wherein each of the plurality of hooks includes an upper end having a second guiding surface extending to a front side and a rear side of each of the plurality of hooks.

7. The sterile adapter according to claim 3, wherein each of the plurality of hooks includes a lower end having a vertical positioning portion on a front side of each of the plurality of hooks.

8. The sterile adapter according to claim 3, wherein each of the plurality of hooks includes a lower end having a slope surface on a rear side of each of the plurality of hooks.

9. The sterile adapter according to claim 3, wherein each of the plurality of hooks includes a lower end having a fitting portion on each of a left side and a right side of each of the plurality of hooks.

10. The sterile adapter according to claim 1, wherein the planar surface is substantially perpendicular to the upper surface of the body structure.

11. The sterile adapter according to claim 10, wherein the lower limiting section has a plane parallel to the planar surface.

12. The sterile adapter according to claim 1, wherein the respective indentation has an upper section and a lower section located below the upper section in a third direction;

a width of the upper section in the first direction is greater than a width of the lower section in the first direction;

wherein the third direction is a top-to-bottom mounting direction of the surgical instrument, and the third direction traverses both the first direction and the second direction.

13. The sterile adapter according to claim 12, wherein in the third direction, the width of the upper section gradually decreases and the width of the lower section is constant.

14. The sterile adapter according to claim 12, wherein the lower limiting section is located below the upper beveled section in the third direction, and the upper beveled section and the lower limiting section are in continuous smooth transition.

15. The sterile adapter according to claim 12, wherein a width of the upper beveled section in the first direction gradually increases in the third direction, such that the width of the upper beveled section is less than a width of the lower limiting section;

the lower limiting section has a constant width in the first direction.

16. The sterile adapter according to claim 12, wherein the upper beveled section has a smoothly transitioned curved surface;

an intersection line between the upper beveled section and any plane parallel to a plane defined by the first direction and the second direction is a straight line parallel to the planar surface.

17. The sterile adapter according to claim 12, wherein the lower limiting section is parallel to the planer surface, and a distance between the upper beveled section and the planer surface in the second direction gradually increases in the third direction and is less than a distance between the lower limiting section and the planer surface in the second direction.

18. The sterile adapter according to claim 1, wherein the side wall is substantially perpendicular to the planar surface.

19. A sterile adapter operable with a surgical instrument, comprising a body structure and a backboard configured to be coupled to a back end of the surgical instrument;

wherein the backboard is perpendicular to an upper surface of the body structure, the backboard is provided with a protrusion configured to fit with a corresponding groove at the back end of the surgical instrument, the protrusion protruding from a planar surface of the backboard;

the protrusion has two side walls configured to guide position adjustment of the surgical instrument in a first direction and to limit movement of the surgical instrument in the first direction;

the protrusion further has a guiding surface connecting the two side walls, the guiding surface having an upper beveled section configured to guide the surgical instrument to move in a second direction, and a lower limiting section configured to limit movement of the surgical instrument in the second direction;

the first direction traverses the second direction; and a plane defined by the first direction and the second direction is parallel to the upper surface of the body structure.

20. A surgical robot, comprising an instrument drive;

a sterile adapter operable with a surgical instrument, wherein the sterile adapter comprises a body structure and a backboard configured to be coupled to a back end of a surgical instrument, the backboard is perpendicular to an upper surface of the body structure, the backboard has a surface defining two indentations spaced apart from each other and a guiding surface between the two indentations, a respective indentation of the two indentations is configured to accommodate a corresponding protrusion at the back end of the surgical instrument and has a planar surface configured to limit the corresponding protrusion from moving in a direction perpendicular to the planar surface, and a side wall connecting the planar surface and the guiding surface, the side wall is configured to guide position adjustment of the surgical instrument in a first direction and to limit movement of the surgical instrument in the first direction, the guiding surface has an upper beveled section and a lower limiting section, the upper beveled section is configured to guide the surgical instrument to move in a second direction, the lower limiting section is configured to limit movement of the surgical instrument in the second direction, the first direction traverses the second direction, and a plane defined by the first direction and the second direction is parallel to the upper surface of the body structure; and a surgical instrument having a back end coupled to the instrument drive through the sterile adapter, the back end of the surgical instrument being provided with two protrusions, and each of the two protrusions being fitted into a respective one of the two indentations.

* * * * *